US009928586B2

(12) United States Patent
Burnett et al.

(10) Patent No.: US 9,928,586 B2
(45) Date of Patent: Mar. 27, 2018

(54) DEVICES AND METHODS FOR DETERMINING MENSTRUAL BLOOD LOSS

(71) Applicant: TheraNova, LLC, San Francisco, CA (US)

(72) Inventors: Daniel R. Burnett, San Francisco, CA (US); Marcie Hamilton, San Francisco, CA (US); Evan S. Luxon, Lincoln, NE (US); Robert Odell, Renton, CA (US)

(73) Assignee: TheraNova, LLC, San Francisco, CA (US)

( * ) Notice: Subject to any disclaimer, the term of this patent is extended or adjusted under 35 U.S.C. 154(b) by 89 days.

(21) Appl. No.: 14/935,259

(22) Filed: Nov. 6, 2015

(65) Prior Publication Data
US 2016/0063698 A1    Mar. 3, 2016

Related U.S. Application Data

(63) Continuation of application No. PCT/US2014/043495, filed on Jun. 20, 2014.

(60) Provisional application No. 61/957,052, filed on Jun. 24, 2013.

(51) Int. Cl.
G06T 7/00    (2017.01)
G06T 7/62    (2017.01)
G06F 19/00    (2018.01)

(52) U.S. Cl.
CPC .......... *G06T 7/0012* (2013.01); *G06F 19/321* (2013.01); *G06F 19/345* (2013.01); *G06F 19/3431* (2013.01); *G06T 7/62* (2017.01); *G06F 19/3418* (2013.01); *G06T 2207/30108* (2013.01); *G06T 2210/41* (2013.01)

(58) Field of Classification Search
CPC ....... G06T 7/0012; G06T 7/62; G06F 19/321; G06F 19/3431; G06F 19/345
See application file for complete search history.

(56) References Cited

U.S. PATENT DOCUMENTS

2002/0190982 A1*  12/2002  Kotcheff ................ G06T 17/20
                                                  345/420
2010/0280117 A1   11/2010  Patrick et al.
2011/0244589 A1*  10/2011  Klein ..................... G01N 33/86
                                                  436/164
2013/0010094 A1*  1/2013   Satish .................... G06K 9/00
                                                  348/77
2013/0011042 A1*  1/2013   Satish .................... G06K 9/00
                                                  382/134

* cited by examiner

Primary Examiner — Kim Vu
Assistant Examiner — Molly Delaney
(74) Attorney, Agent, or Firm — Levine Bagade Han LLP

(57) ABSTRACT

A computer application on a device for tracking menstrual blood loss by receiving an image of a used sanitary product, analyzing, or receiving analysis of, the amount of blood volume in the image, and aggregating the blood volume from more than one image to determine total blood loss volume for a menstrual cycle.

68 Claims, 21 Drawing Sheets

Heavy Tampon
Click on the image that most closely represents your tampon
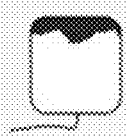
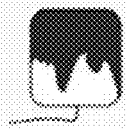
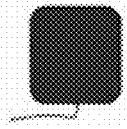
Panty Liner
Click on the image that most closely represents your liner
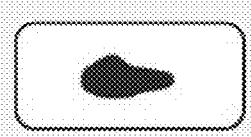
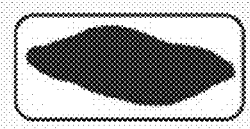
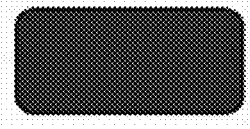
FIG. 7C
FIG. 7D

DEVICES AND METHODS FOR DETERMINING MENSTRUAL BLOOD LOSS

CROSS-REFERENCE TO RELATED APPLICATIONS

This application is a continuation of International Patent Application No. PCT/US2014/043495 filed Jun. 20, 2014, which claims the benefit of priority to U.S. Provisional Application No. 61/957,052 filed Jun. 24, 2013, which is incorporated herein by reference in its entirety.

FIELD OF THE INVENTION

The present invention relates to the measurement of menstrual blood loss.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND

Menorrhagia is a common gynecological complaint. Menorrhagia is defined as menstrual blood loss of >80 ml per menstrual period. This is an objective definition and is felt to represent a loss which, over a period of time, is likely to lead to iron deficiency anaemia. Objective assessment of blood loss is time consuming, not readily available and is not acceptable to the majority of patients in a clinical setting. The alternative subjective assessment is recognized as being an unreliable indicator of true menorrhagia. Higham in 1990, reported the use of a validated pictorial blood loss assessment chart in an attempt to provide a simple, accurate method of assessment of menstrual blood loss.

The chart records not only the number of towels and tampons used, but also takes into account the degree to which individual items were soiled with blood, and the passage of clots and associated flooding. From this chart it is possible to provide a score for each menstrual cycle. Using the Higham chart, a score>100 has a sensitivity of 86% and a specificity of 89% for the diagnosis of menorrhagia. The chart has been validated by correlating the pictorial chart score and the menstrual blood loss in ml using an alkaline haematin method for determination of menstrual blood loss.

The Higham chart has become the most commonly used pictorial chart. In their study they required patients to use the same type of internal and external protection (Tampax® and Kotex® Fems super plus tampons and Kotex® simplicity size 2 towels). The reason for this is that the capacity of different products to absorb blood varies widely and for this reason one of the conclusions of the paper is that the use of different sanitary protection may limit the use of the Higham pictorial chart. The chart can still be useful in clinical trials providing all the patients in the study are provided with the same sanitary protection. This allows for a direct comparison before and after medical intervention, but due to the potential differences in product absorption, does not allow a comment with regards the diagnosis of menorrhagia based on the Higham findings of a score of 100 (which represents 80 ml menstrual loss).

While the Higham chart was an advance that allowed patients to record their own blood loss in a user-friendly manner that didn't require collection of used menstrual product (as with alkaline hematin), the use of the Higham chart has been found to be unreliable due to the variation in the ability of the individual patients to score their own menstrual product.

What is needed, then, is an easy to use, outpatient method for the determination of menstrual blood loss in a reliable, accurate and precise manner.

SUMMARY

The majority of the issues with the Higham chart (or PBAC) are related to the requirement that each patient record their own used menstrual product. The present invention remedies this failure by allowing for objective review of the patient's menstrual blood loss by a third-party reviewer and/or by a computer application.

Generally, one method for tracking menstrual blood loss volume may comprise receiving one or more images of a used sanitary product from a first client device, displaying the one or more images on a second client device, receiving at least one input from a user via the second client device which includes an estimate of blood volume within or upon the sanitary product in the one or more images, and aggregating blood volume data from the one or more images to determine blood loss volume via a microprocessor for at least one menstrual cycle.

In yet another method which may be automated for tracking menstrual blood loss volume via computer, the method may generally comprise receiving one or more images of a used sanitary product from a first client device, analyzing the one or more images via a microprocessor to estimate blood volume in the one or more images, and aggregating blood volume data from the one or more images to determine blood loss volume via the microprocessor for at least one menstrual cycle.

Such methods may utilize non-transitory computer-readable storage medium having instructions stored therein, which when executed by a microprocessor, causes the microprocessor to perform the methods for tracking menstrual blood loss volume.

In some embodiments, the present invention allows for a patient to take a photograph or other image of their used menstrual product, ideally on a standardized and/or labeled background, or mat, then discard the product as they normally would. The patient may, optionally, fill out a diary to indicate whether they had flooding and/or clotting. Any clots may also be added to the labeled background material and any flooding may also be captured with the same or another image. In some embodiments, a Wi-Fi or cellular data enabled device is used to capture the images of used product, data, clots and/or flooding and upload the data to a server with appropriate privacy controls, for example HIPAA or other regionally based privacy controls. This prompt upload of images allows for clinicians and/or investigators to track patient compliance with photographing or otherwise imaging their used product. The application may also prompt the user to ensure that she is recording all the necessary information, and/or doing so on a cyclic basis.

In some embodiments, the images of used menstrual product, data, and/or clots and/or flooding episodes may then be read by a centralized or remote reviewer or reviewers to provide consistency, accuracy and precision of menstrual blood loss readings.

In some embodiments, the images of used menstrual product, data, and/or clots and/or flooding episodes may be automatically analyzed by a server application system on a server and/or a client application on a client computer or hand held device.

In some embodiments, the images of used menstrual product, data, and/or clots and/or flooding episodes may be analyzed by a combination of a server application system on a server and/or a client application on a client computer or hand held device and centralized or remote reviewer or reviewers.

The present invention has excellent applicability, in particular, to clinical studies. In this setting, one or more reviewers can review all of the images and score them based on their appearance. Any discrepancies can be resolved with a third reviewer. The review of all images may be achieved at the same time, as well, and randomized to ensure that the reviewer is not aware as to whether they are reviewing a baseline or follow-up image. This allows for consistency of readings and true blinding of the reviewer of the images.

The present invention also has applicability to home use, outside of a clinical trial. For example, a personal physician may ask his/her patient to track blood loss over a period of time to determine appropriate treatments, diagnoses, etc.

In some embodiments, the sanitary product is placed on a specialized background or mat. This may increase the quality of the image, including the contrast of the blood with the background. The mat may have calibrating marks and/or figures to aid in measurement of the sanitary product, amount of blood on the sanitary product, color or blood on the sanitary product, density of color and/or range of color on the sanitary product, and/or amount and/or color and/or density of blood on the mat separate from the sanitary product, for example clots and flooding. Marks and/or figures on the mat may also help identify skew, scale, angle and/or lighting of the image. Marks and/or figures on the mat may also identify the user, the type and/or brand of sanitary product, the date, the time, the location, etc. of the sample and the image taken.

The mat may be non-reflective on one side and waterproof or water resistant on the other side, so that flash photographs or other images may be taken of the non-reflective side, preventing glare in the images, while the waterproof side prevents leakage of fluids including blood. The non-reflective side may also be absorbent to absorb blood and other fluids. The mat may be crinkle or wrinkle resistant. The mat may be disposable or reusable, but is preferably disposable. The mat may have tape strips or other adhesive technologies incorporated into the mat so that the mat can be rolled or folded with the soiled sanitary product enclosed.

In some embodiments, the mat may be transparent so that images can be taken of all sides of the sanitary product. For example, in using a sanitary pad, a large area of the top side of the pad may be soaked with blood, where only a small area of the bottom side may be soaked with blood. In this situation estimation of the blood volume in the pad may be aided by incorporating both the top blood surface area and the bottom blood surface area (as well as other possible factors) in the determination of blood loss. Pictures may also be taken of more than one side of the sanitary product.

In some embodiments, the sanitary product may be compressed for imaging. For example, a transparent object may be placed on top of the sanitary product to compress it, and/or even out the thickness. For example a radially expanding tampon may be placed end down (string up) on a mat, and a clear object, such as glass, plexiglass, etc. may be placed on top of the tampon forcing it to expand radially. In this way, all of the outside surfaces of the tampon are visible in one image, and a better estimate of the amount of blood can potentially be made. In another variation, the compression need not be performed with a clear material, if the compressing material is removed after compression. In other words, the tampon may be "mashed" with an object and then the object removed and an image captured. This type of compression or reorientation may be done with any of the sanitary products to obtain a better image.

In some embodiments other tools may be used to flatten, spread, contain, organize, or in any way orient the sanitary product so that an accurate determination of blood volume can be obtained from the image of the sanitary product.

In some embodiments, the standardized background, or mat, may have a grid or other demarcations for size and/or skew reference, one or more colors for color-balancing and/or a unique identifier for each patient and/or an identifier of the menstrual product used. In some embodiments a clinician or lay person may perform the reading or the reading may be automated and computerized or the analysis may be performed by a combination of both automatic analysis and human review.

In addition to a grid, other patterns and/or markings may be incorporated into the mat. These include circles, squares, grids, patterns, rulers, concentric shapes, colors, color scales, darkness scales, etc. The mat may also be textured to help with absorption and/or to help identify and/or minimize shadows in the image.

Standard or calibrating images may be used to compare to user images. Calibrating images may be taken using the same mat configuration with various brands and versions of sanitary products with known amounts of blood. Calibrating images may be taken under different conditions including different lighting, angles etc.

In some embodiments, the camera is equipped with an infrared filter, which increases the contrast of the blood in order to more easily estimate volume. An infrared light source may also be used to further enhance this effect.

In some embodiments, a compound may be applied to the menstrual product before the picture is taken in order to increase the contrast of the blood. One example of such a product is Luminol, which demonstrates chemiluminescence when it comes in contact with the iron in hemoglobin.

In some embodiments, the volume of menstrual blood loss is measured by means of a weight/mass scale. In its preferred configuration, the scale comes with standardized bags or containers that the menstrual product is placed in prior to reading. The scale is preferably handheld, and may connect to a Wi-Fi or cellular enabled device, such as the user's cell phone. Thus, each measurement can be sent to the server or physician in real-time, which may assist in compliance-tracking and real-time evaluation of the data.

The potential for automation and computerization of the image readings represents a major clinical advantage. Without the need for a person reviewing the images, the procedure is less labor intensive, allowing patients to be screened prior to any abnormal uterine bleeding procedure to ensure that they truly have abnormal uterine bleeding. Patients undergoing global endometrial ablation, drug-eluting IUD insertion and/or hysterectomy now are not screened due to lack of reliability of metrics (ie PBAC) and the onerous and costly nature of screening (alkaline hematin). It is well known in the literature, though, that a patient's subjective assessment of whether they have abnormally heavy bleeding is highly inaccurate. It is anticipated that the present invention would streamline the menstrual blood loss determination process to such a degree that it would be used prior to any of the above-mentioned procedures in order to determine patient eligibility. This would help ineligible patients to avoid an unnecessary procedure and help definitively determine that eligible patients truly do have heavy uterine bleeding.

In some embodiments, the present invention would allow for the immediate upload and processing of images based on a computerized process that is calibrated to the particular menstrual products used by each woman. The ability to determine menstrual blood loss on a variety of products is also beneficial. Each product type may be validated for use with the present invention. Thus, yet another aspect of this invention is the described method of calibrating images to menstrual blood loss for each individual menstrual product.

Below is a possible calibration protocol which can be performed using the present invention. The aim of this sample protocol is three fold:

AIM

Aim 1. Product Standardization—To assess the amount of time-expired blood required to produce the same appearances depicted on the Higham chart to allow the standardization of the products.

Aim 2. Validate Higham Score as a Reliable Indicator of Menstrual Blood Loss—To determine the precision of gynecologist readings of time-expired blood soiled products.

Aim 3. Validate Higham Scoring of Photographs as an Indicator of Menstrual Blood Loss—To determine the extent to which gynecologist readings of time-expired blood soiled products correlate with gynecologist readings of photographic images of the same time-expired blood soiled products.

The methods for this sample protocol include using 3 clinicians to evaluate the products. Multiple products may be used and identified for the standardization. For example, several products manufactured by a single manufacturer may be used.

METHODS

Aim 1. Product Standardization

Time expired blood may be added to each of the products in 0.5 ml increments until both a minimum volume and maximum volume are determined to depict a maximum score for both the pads and towels. Maximum volume may be the volume at which the product starts to leak on movement. This allows the mean volume required to produce a maximum score to be determined. These data may then be used to calculate an adjustment score for each individual product to allow for an accurate reading of actual blood volume using the Higham chart scoring system.

Aim 2. Validate Higham Score as a Reliable Indicator of Menstrual Blood Loss One clinician may add known volumes of time expired whole blood to the product in increments of 0.5 ml to produce appearances depicted on the Higham chart and each product may be photographed on a standardized background or mat. The pads and tampons may be placed in a random fashion so that it is not possible to try and predict the next score. The two other clinicians (reviewers or readers) may then be asked to score the products based on the Higham chart to see if there was an agreement between them, but they may be kept blinded to the actual volumes required to produce the appearances and to the previous clinicians score. Two readers may be chosen and blinded to ensure that the test is reproducible and that there is not a wide variation in the volume of blood required to achieve each score.

Aim 3. Photographic Scoring

One week after the completion of Aim 1 each of the three clinicians may be asked to score the products based solely on the photographic images taken of the individual product during Aim 1. The product may be presented in a randomized order to prevent pattern recognition so that it is not possible to try and predict the next score.

DATA ANALYSIS

Aim 1. Product Standardization

The average amount of blood required to reproduce the Higham chart appearances may be calculated for each product. These averages may then be used to create an adjustment factor for each product at each score. These adjustment factors may allow for the accurate measurement of blood loss with new menstrual products with different absorbencies and appearances when compared to the products used in the initial Higham chart.

Aim 2. Validate Higham Score as a Reliable Indicator of Menstrual Blood Loss A Pearson Correlation coefficient may be calculated to determine: 1) the degree of correlation between the actual blood volume and the readings for each clinician, and 2) the degree of correlation between the actual blood volume and the average reading for both clinicians.

Aim 3. Photographic Scoring

Photographic readings may be compared to readings obtained in Aim 1 for each reading clinician to determine the extent of agreement. A Pearson Correlation coefficient may also be calculated to determine: 1) the degree of correlation between the actual blood volume and the photographic readings for all three clinician, and 2) the degree of correlation between the actual blood volume and the average photographic readings for all three clinicians.

The sample protocol above is only an example and several different protocols may be used to validate and/or calibrate sanitary products and/or blood loss. Calibration and/or validation may be performed by the application system, manually, or a combination of both.

BRIEF DESCRIPTION OF THE DRAWINGS

FIGS. 7A-7J show possible screen configurations of a user application.

DETAILED DESCRIPTION

Figure 1A:
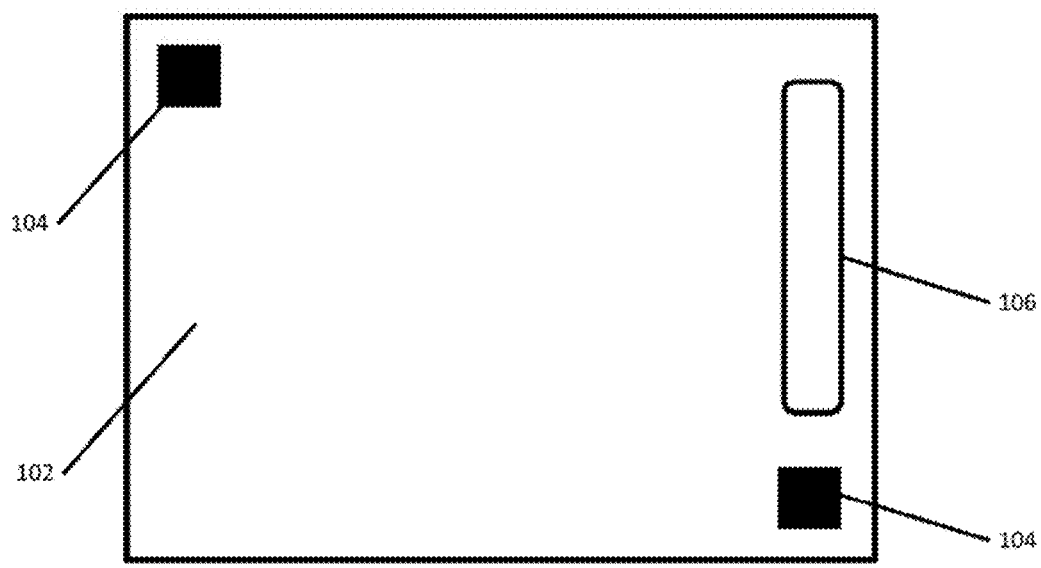
FIGS. 1A-1R shows various embodiments of mats.

Various devices and methods for determining menstrual blood loss are provided. In some embodiments, various devices and methods may include analyzing images of used sanitary products taken while the sanitary product is on a matt. The images may be analyzed to determine how much blood is in the sanitary product, and/or in clots and/or in flooding and/or lost in any other form due to menstruation. The blood volume analysis may be performed on individual images and the individual blood volume analysis may be aggregated and/or analyzed across several images, to represent blood loss via multiple products, over multiple days and/or over multiple cycles. Data may also be aggregated and/or analyzed across multiple patients.

The blood volume analysis may be performed automatically, via a computer system, or visually, via reviewers viewing the images, or a combination of both automation and reviewers. Automatic analysis may include image adjustment, for example, for scale, lighting, angles, colors, darkness, lightness, blurriness etc. Automatic image analysis ma also include image segmentation, for example separating components of an image, for example, the following components may be separated for analysis: background matt, sanitary product, dry sanitary product, wet sanitary product, bloody sanitary product, shadows, artifacts, darker blood, lighter blood, body fluids, mucus, colors, tags, labels, calibrating marks, other marks, measurements, product ID, user ID, color depth, etc. Image analysis techniques may include edge detection, convolution, deconvolution, object recognition, masking, subtraction, algebraic modification, Fourier transforms, averaging, and/or stain detection using color, color depth, color darkness/lightness or other thresholds, or any other image analysis technique. Image analysis may account for shadows or other artifacts. Blood clots and/or blood flooding may be detected and analyzed either automatically or manually.

The automated analysis of blood volume may be checked by users or reviewers. Alternatively, the analysis may be done in part or entirely by reviewers or entirely by the computer application.

In some embodiments a software application guides the patient or user through the data input and sanitary product imaging process. The application may remind the user when it is time to enter data and/or an image. The application may prompt the user to enter product information, as well as other data such as the user's perspective on blood loss, the existence of blood clots, blood clots size, blood flooding, blood flooding amount, blood leakage, blood leakage amount, symptoms, date, time, time in cycle, etc.

The application may aggregate data over more than one data entry, either for one patient, or across more than one patient, and analyze this data for trends. These trends might include cycle length, blood loss over time, blood loss frequency, blood loss relationship to day of cycle, blood loss relationship to symptoms, users' perception of blood loss relationship to imaging analysis of blood loss, different sanitary products' relative absorbency, sanitary products' relative accuracy for identifying blood volume, etc. This information may be used by the application, for example, the application may prompt a user to enter data when her specific cycle period is approaching. Or the application may alert administrators of the application that certain sanitary products are less accurate than others in terms of determining blood volume lost. Data may also be used for analysis including trend analysis.

In some embodiments a 3D camera may be used, using technology similar to that of a CT scanner, MRI scanner, Ultrasound scanner etc., and/or using non-radiation based visible 3D technology. In these embodiments, the image may be analyzed in a volumetric manner, allowing the system to segment the blood volume and determine very accurately the volume of blood in a sanitary product.

Figure 1B:
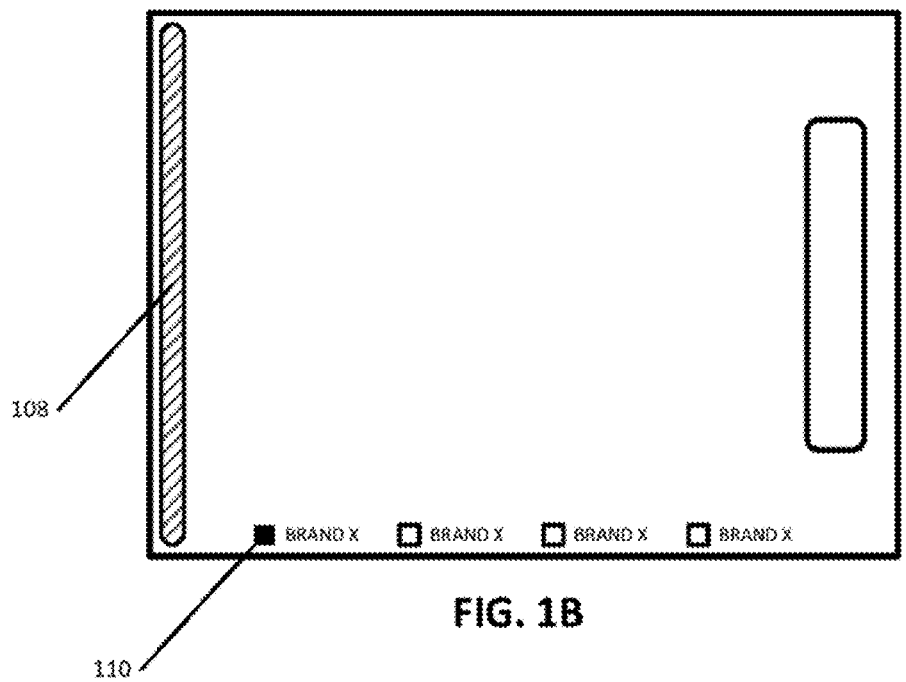
Figure 1C:
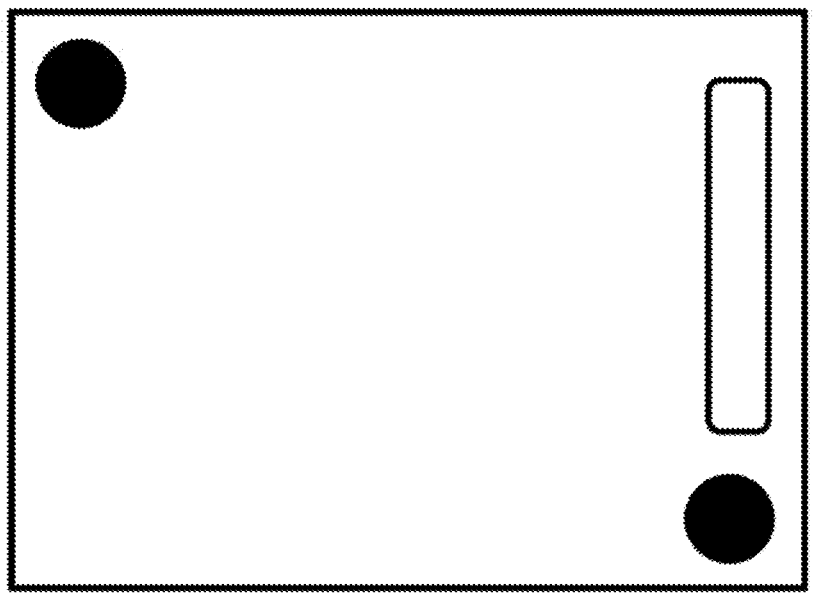
Figure 1D:
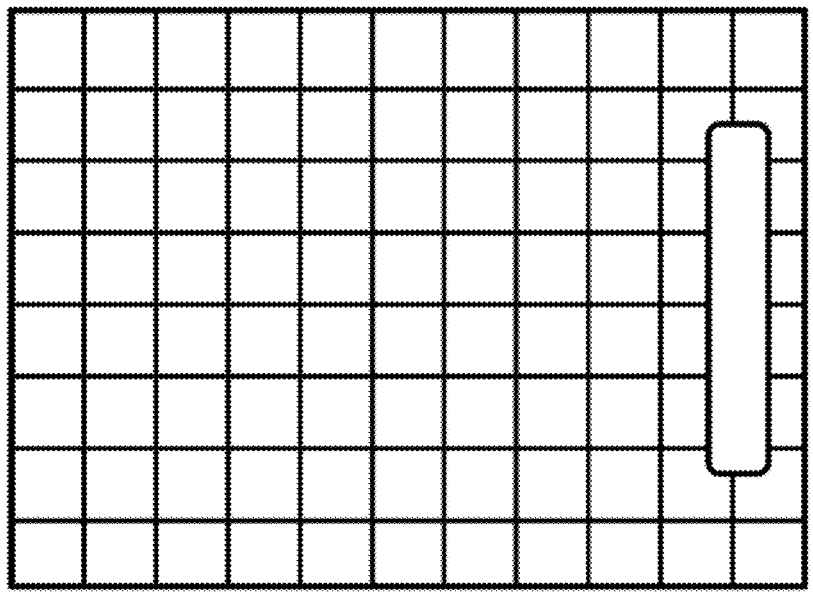
Figure 1E:
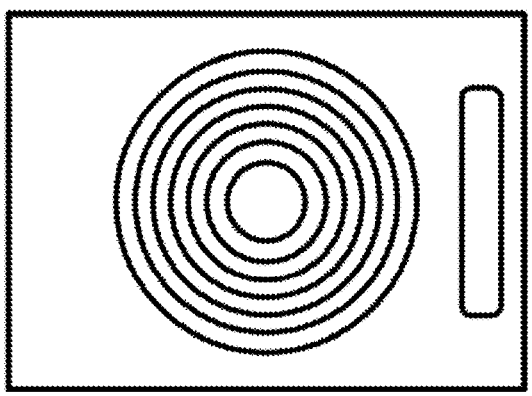
Figure 1G:
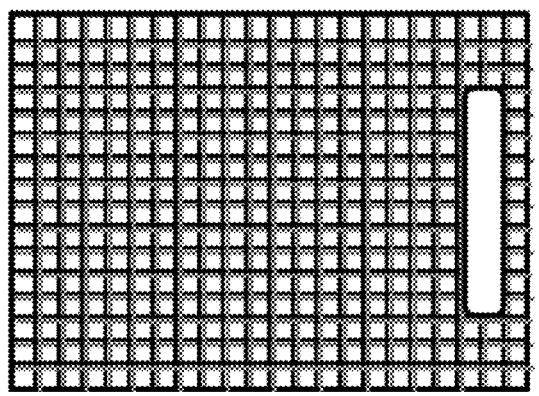
Figure 1F:
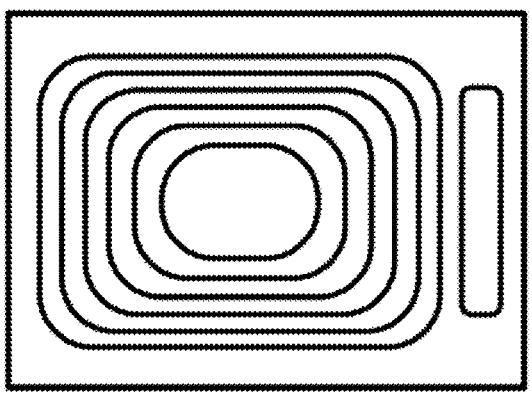
Figure 1H:
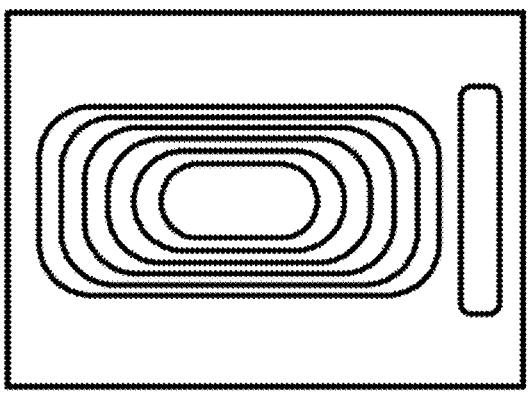
Figure 1I:
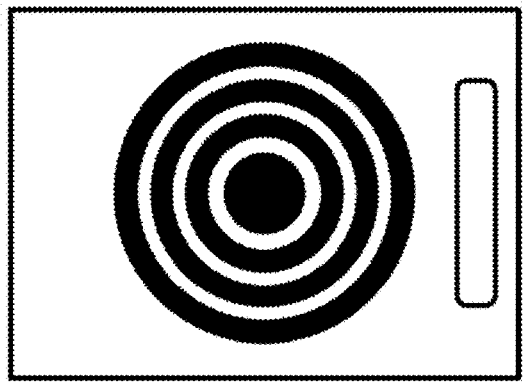
Figure 1J:
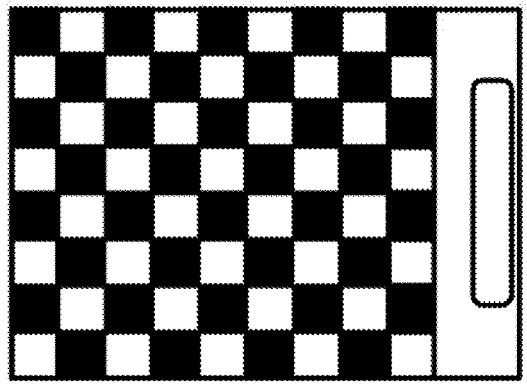
Figure 1K:
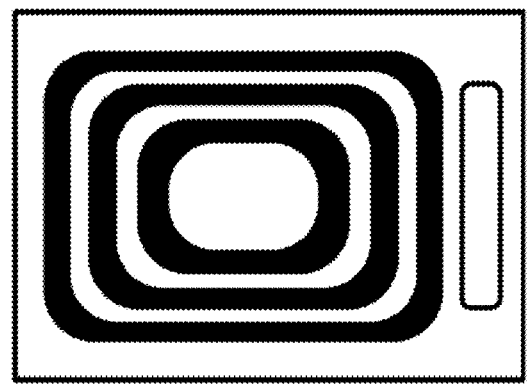
Figure 1L:
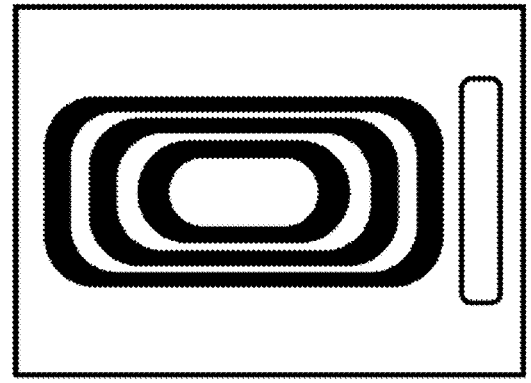
Figure 1M:
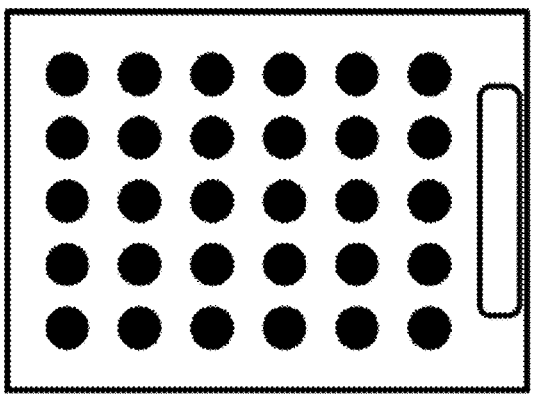
Figure 1N:
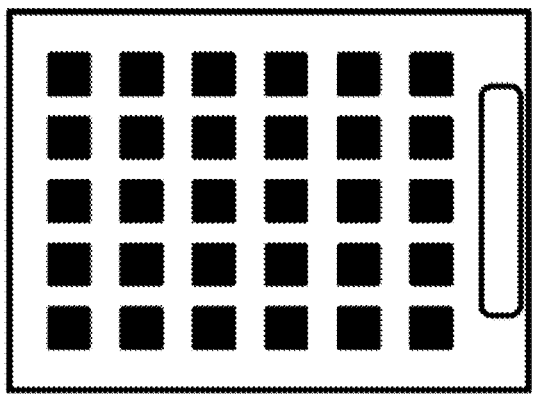
Figure 1O:
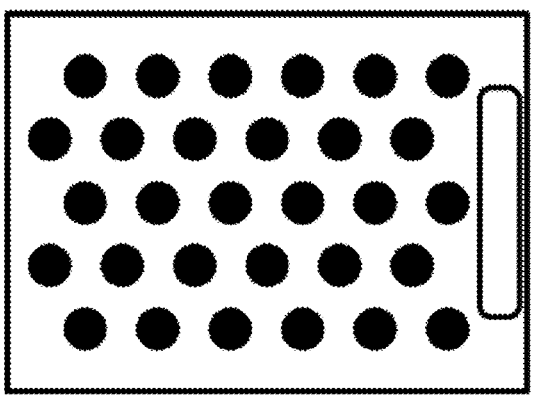
Figure 1P:
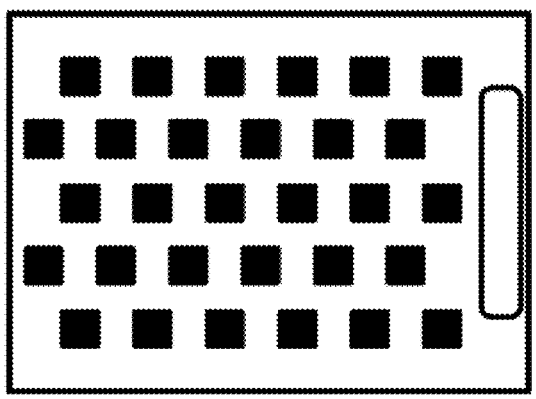
Figure 1Q:
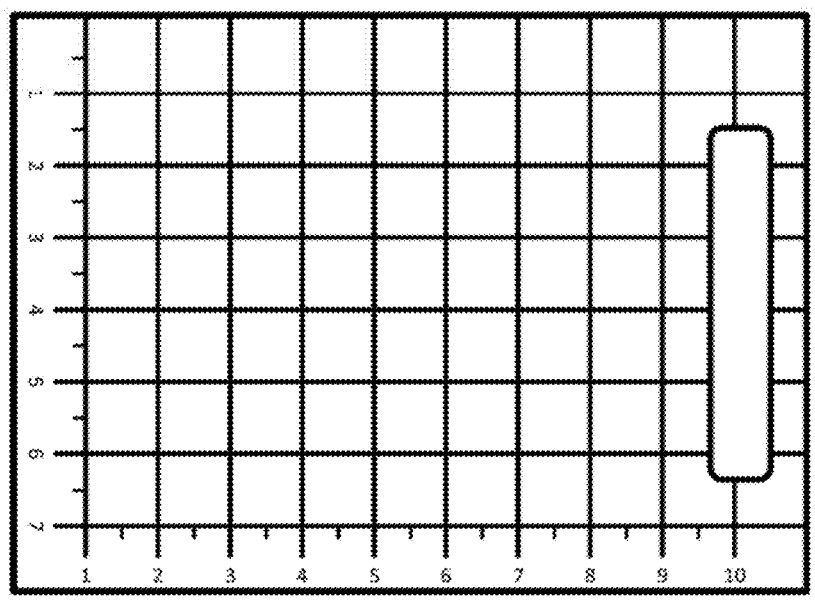
Figure 1R:
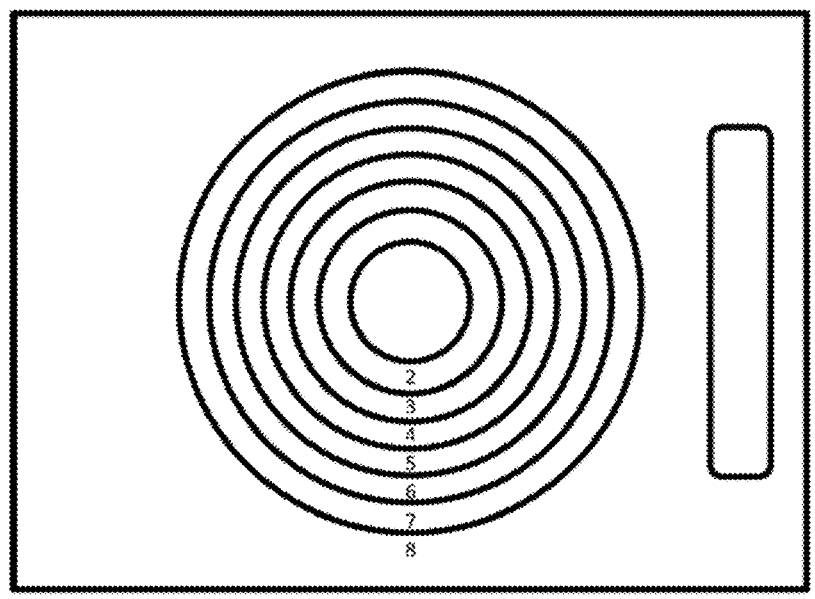

FIGS. 1A-1R show possible embodiments of a mat. A mat may be used to photograph or otherwise obtain an image of a sanitary product, primarily used sanitary products, although unused sanitary products may also be imaged for identification and calibration purposes. Used sanitary product is placed on the mat for imaging. The image may be taken with any camera or image collection device, but may be taken with a mobile device camera (e.g., cameras integrated with wireless mobile devices such as smartphones, tablets, etc.) so that it can be integrated directly into an application on the mobile device. However, any camera can be used, including more advanced 3D imaging system.

FIG. 1A shows a possible embodiment of a mat. Shown is base 102 which may be made out of a non-reflective absorbent material. Markings 104 in this embodiment are square or rectangular although the markings 104 may embody other shapes or forms. These markings may be used to determine scale, skew, color, or other characteristics of the image mentioned herein. Label or label area 106 may be used to identify the user, product, date, or other attribute of the sample and/or data. A label may be pre-affixed to the mat or a label may be placed on the mat before, during or after the sample is placed on the mat for imaging. The label may be placed before imaging the mat with the sanitary product so that the information on the label may be incorporated into the image analysis.

FIG. 1B shows a possible embodiment of a mat. Adhesive strip 108 is shown. In this embodiment, a used sanitary product can be placed on the mat, imaged, and subsequently rolled or folded so that the used sanitary product is enclosed inside the rolled or folded mat. Strip 108 can be used to secure the mat in the folded or rolled state. A strip is shown here, but other embodiments can be used, such as one or more adhesive spots, clips, etc.

In addition, a mat may be capable of being marked by the patient, with name, date, etc. This could be in the form of a check off (machine readable) or free text entry, or other suitable manner. Selection box 110 is an example of this feature. This feature could be used to identify sanitary product brand, type, or other attribute. Any relevant data may be captured in this manner, and may be automatically analyzed by the application.

FIG. 1C shows a possible embodiment of a mat where the markings are circles instead of squares or rectangles. Any shape can be used, however.

FIG. 1D shows a possible embodiment of a mat where the markings include a grid. The grid may be uniformly spaced apart from one another at predetermined distances, e.g., to provide a scale for comparison, or they may be provided to assist with orienting the sanitary product for image capture or post processing purposes. Alternatively, the grid may be arbitrarily spaced apart from one another while still maintaining a transverse orientation between the lines.

FIG. 1F shows a possible embodiment of a mat where the markings include concentric circles or ovals. Again, the radial distances between the concentric circles or ovals may be predetermined or arbitrary.

FIGS. 1F and 1H shows possible embodiments of a mat where the markings include concentric shapes, in this case rounded rectangles, although any shape can be used.

FIG. 1G shows a possible embodiment of a mat where the markings include a textured grid. The texture may be in the mat itself, similar to a dentist's bib, where one side of the mat is a non-reflective absorbent surface, and the other side is waterproof.

FIGS. 1I-1L shows possible embodiments of a mat where the markings include various shapes. The darker areas in any embodiment may be black, or they may be color.

FIGS. 1M-1P shows possible embodiments of a mat where the markings include various patterns which may be uniformly spaced apart from one another, e.g., in a grid-like pattern or staggered pattern. Moreover, although circles and squares are shown, the markings may be formed in any number of shapes and sizes. Additionally, the shapes may be uniform or they be embodied in different shapes upon the same mat in repeating patterns or an arbitrary pattern. The darker areas in any embodiment may be black, or they may be color.

FIGS. 1Q and 1R show possible embodiments of a mat where the markings include one or more dimensional scales. The scales may be in any dimension, including inches, centimeters, millimeters, degrees, etc. The scales may be linear or radial or in any other configuration. The scales may be configures to be automatically read and analyzed by the application when analyzing the images.

Figure 2:
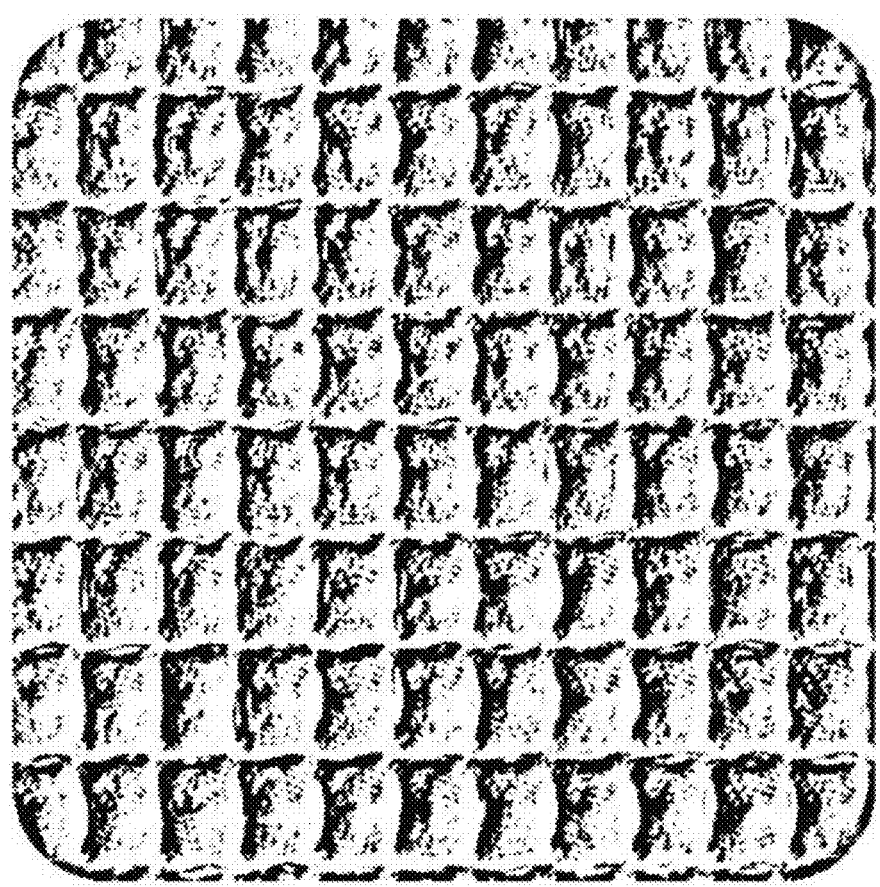
FIG. 2 shows detail of an embodiment of a mat.

FIG. 2 shows detail of a possible embodiment of a mat where the mat material is textured.

Figure 3A:
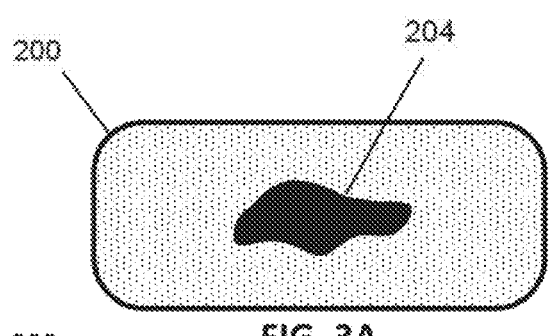
FIGS. 3A-3C shows various representations of a sanitary pad.
Figure 3B:
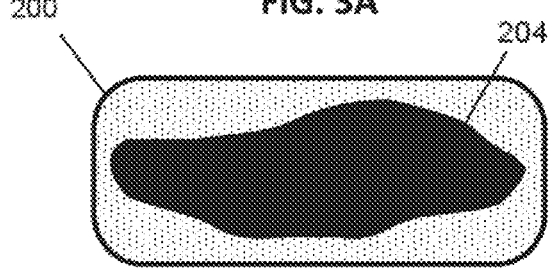
Figure 3C:
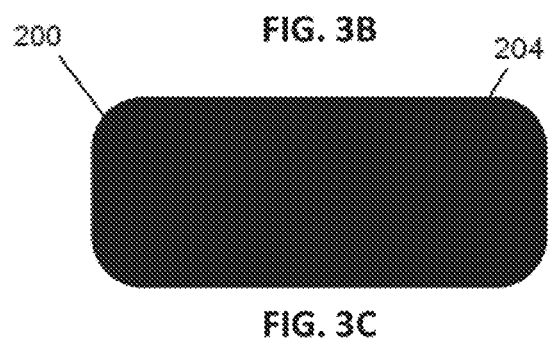

FIGS. 3A-3C show graphic representations of used sanitary pads 200 with various levels of blood (or other bodily fluids) 204 soiling the pad 200. FIG. 3A shows a lightly soiled pad, FIG. 3B shows a medium soiled pad, and FIG. 3C shows a heavily soiled pad.

Figure 4A:
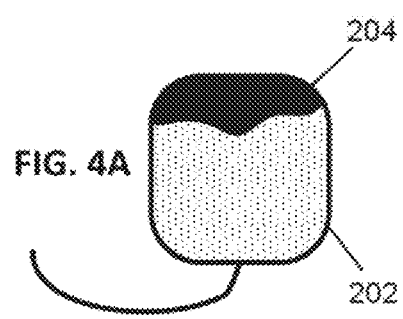
FIGS. 4A-4C shows various representations of a tampon.
Figure 4B:
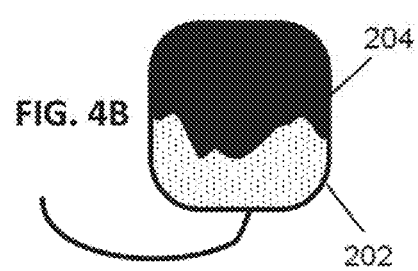
Figure 4C:
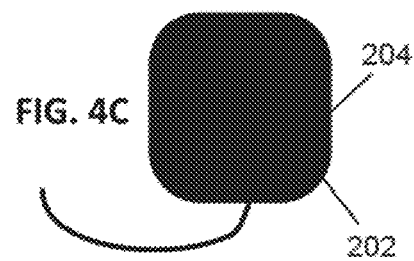

FIGS. 4A-4C show graphic representations of used tampons 202 also with various levels of blood 204 soiling the tampon 202. FIG. 4A shows a lightly soiled tampon, FIG. 4B shows a medium soiled tampon, and FIG. 4C shows a heavily soiled tampon. Graphic figures like these may be used in some embodiments of the application so that a user, or a reviewer, can categorize either images of, or actual, soiled sanitary products.

Figure 5A:
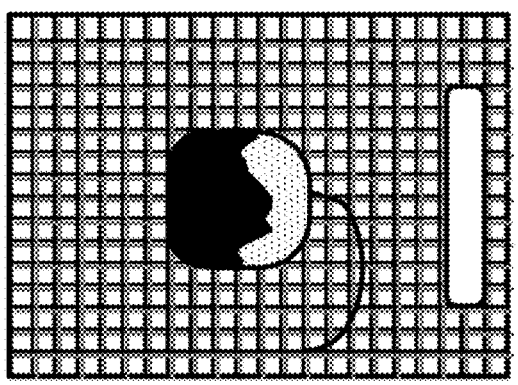
FIGS. 5A-5D shows various representations of sanitary products on mats.
Figure 5B:
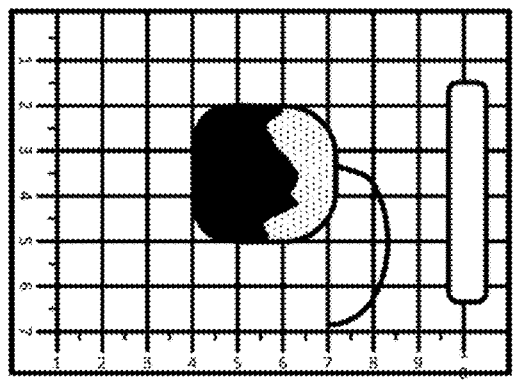
Figure 5C:
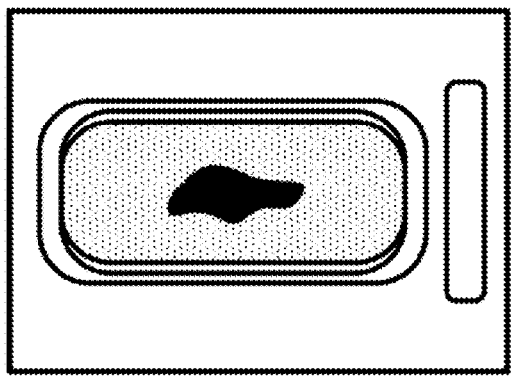
Figure 5D:
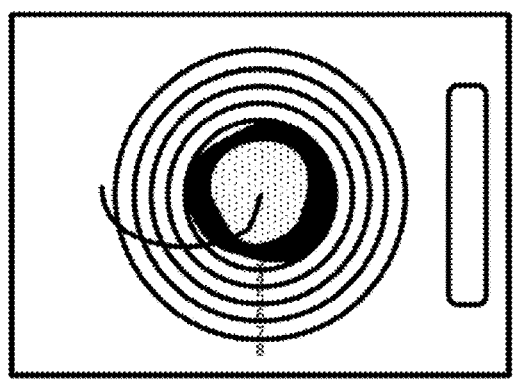

FIGS. 5A-5D show representations of soiled sanitary products on various mat embodiments. The markings on the various embodiments help identify the size and shape of the sanitary product, as well as the amount of blood absorbed by the sanitary product. FIGS. 5A and 5B show a soiled tampon lying sideways on a mat. FIG. 5C shows a soiled sanitary pad on a mat. FIG. 5D shows a soiled tampon lying string up on a mat. Since the blood absorbed by a sanitary product may not be evenly distributed, the sanitary product may be imaged in any position on the mat. In some embodiments, the sanitary product may be imaged in more than one position, or from more than one angle. Furthermore, any of the various mat embodiments may be used for imaging the sanitary products in any number of positions and/or angles in any number of combinations or embodiments.

Figure 6:
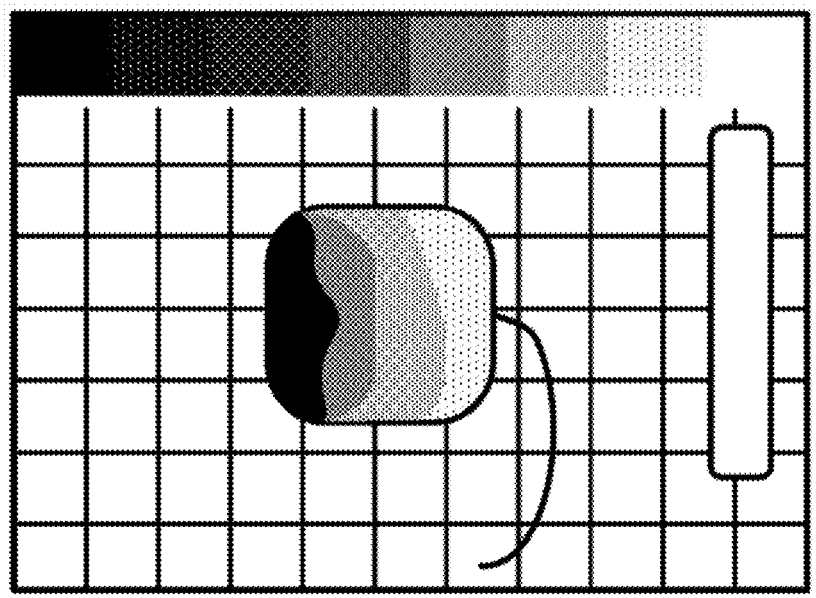
FIG. 6 shows a representation of a sanitary product on a mat.

FIG. 6 shows another possible embodiment. In this embodiment, the mat has color or color depth gradations. These gradations may help the application analyze the image and distinguish among different substances on or in the sanitary product or mat. For example, several substances may be present, including blood, mucus, water, etc. The application can analyze the image and separate these substances based on color, color depth, darkness of color or other factors. This analysis may be performed with or without a mat which has gradations on it.

FIGS. 7A-7J represent screenshots of a possible mobile phone device interface to the application. Although some embodiments may include an application and/or application interface on a mobile phone or other mobile device, embodiments may also include web-based applications, applications on a laptop or desktop computer, applications on tablets, or any other appropriate device. The application may reside on a device, on a server, or a combination of both. The application interface may include a thick or thin client, including a web browser. The device may have a wired or wireless connection to a network, including the internet, an intranet, a local area network using any technology, a point to point network using any technology, a near-field communication method (NFC), etc.

Figures 7A, 7B:
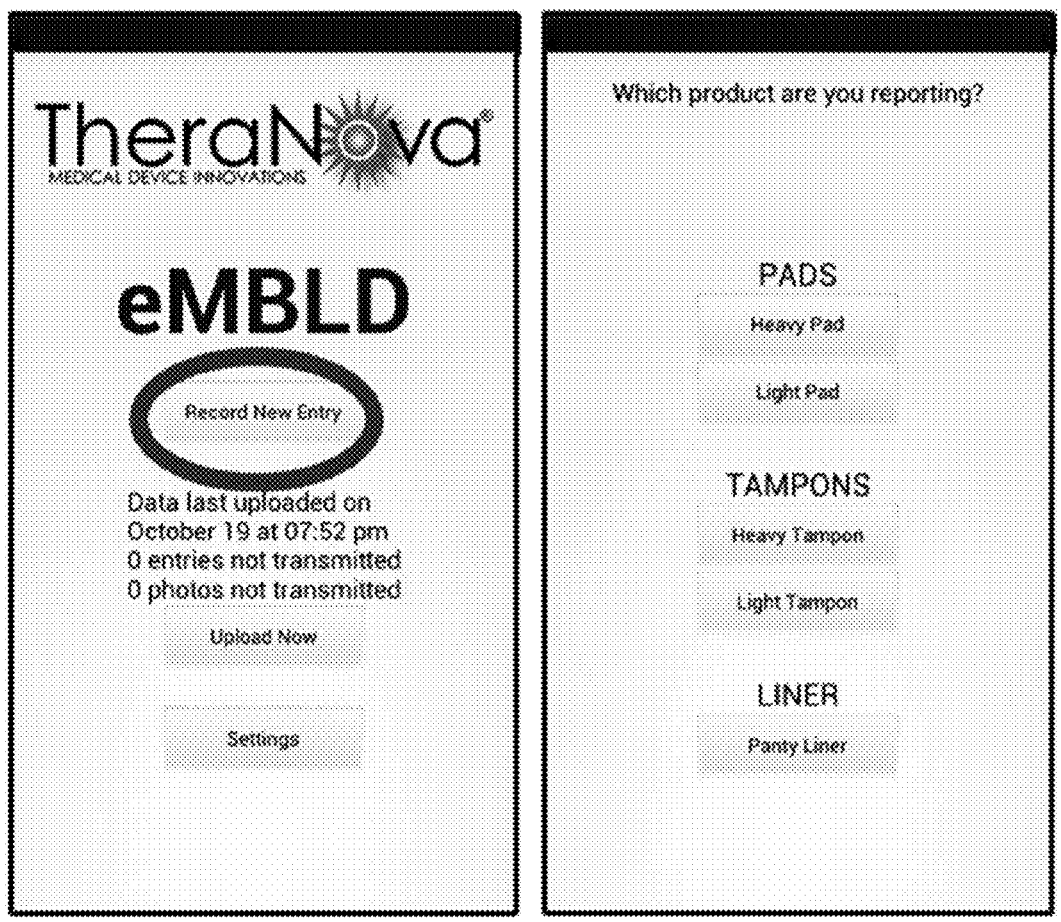

FIG. 7A shows a sample screen of the application interface. The application has displayed various options for the user to select. On this screen the user can choose to record a new entry, upload previously recorded entries, or configure the settings. Previously recorded entries may be waiting for upload, for example, if the mobile device was not in an area with a wireless connection when previous entries were recorded.

FIG. 7B shows a sample screen of the application interface. The application has displayed various options for the user to select. On this screen, the user may choose which type of sanitary product will be recorded. Choices here include a heavy pad, a light pad, a heavy tampon, a light tampon, or a panty liner. Other choices may be displayed here including particular brands and sizes, sample images, shapes, etc. The user may also scan in a bar code, tag or other visual code of the product for analysis by the application. The user may also take a picture of the box or unused sanitary product for product identification by the application. The application may also identify the product from a used sanitary product image. Sanitary product identification analysis may be performed using the shape, length, width, texture, color, string type, string color, or other attribute of the sanitary product. Sanitary product identification may be done automatically, manually, or a combination of both methods.

In some embodiments, the application may limit the user to particular sanitary products and/or types of sanitary products. For example, an application may limit the user to a pad and/or liner and may not allow or support tampons.

FIG. 7C shows a sample screen of the application interface. The application has displayed various options for the user to select. This screen shows three possible blood saturation options for a heavy tampon. A similar screen may be shown for any of the product options. The three images on this screen show a tampon with a small amount of blood, a medium amount of blood and a large amount of blood (e.g., as previously described). The user is instructed to select the image which best represents her used sanitary product. FIG. 7D is a similar screen for a panty liner (e.g., having blood saturation as previously described).

Figure 7E:
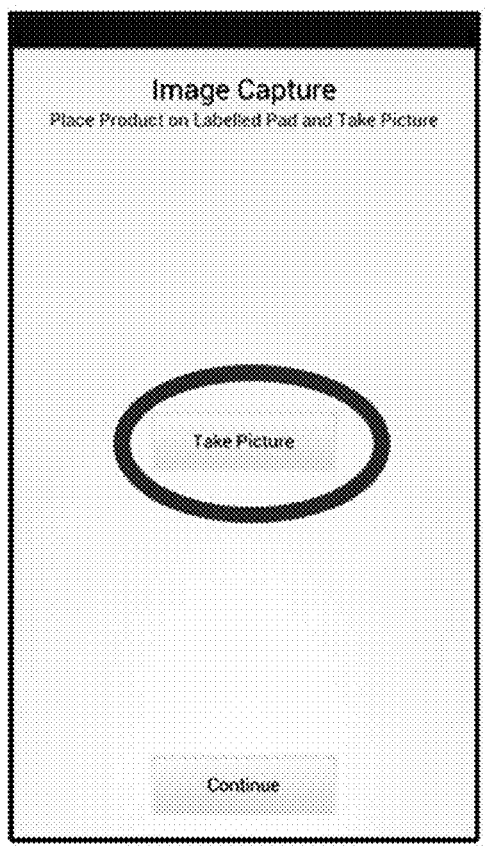

FIG. 7E shows a sample screen of the application interface. The application is prompting the user to take an image of her used sanitary product.

Figure 7F:
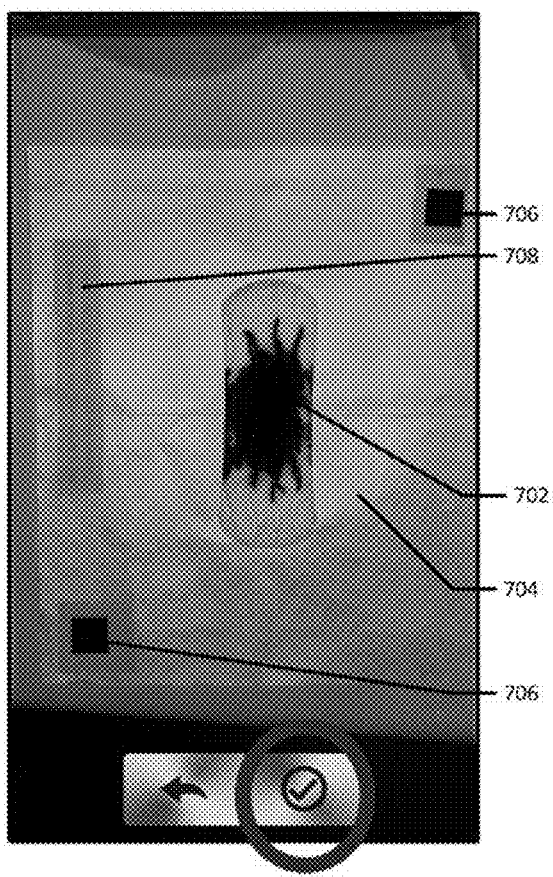

FIG. 7F shows a sample screen of the application interface in which the user has taken an image of used sanitary product 702 along with mat 704 on which the sanitary product is resting. The mat has markings 706 as well as label 708. The markings and/or label may be used by the application in any of the ways described herein. The user is presented options on the bottom of the screen. In this example, the user may choose to accept the image or retake the image. The application may also analyze and accept or reject the image based on certain criteria. The application may control certain parameters of the image, including mandating a flash or other lighting, or controlling focus etc. A platform or frame may be used by the user to take the image to ensure a particular distance and angle from the sanitary product and/or mat.

Figures 7G, 7H:
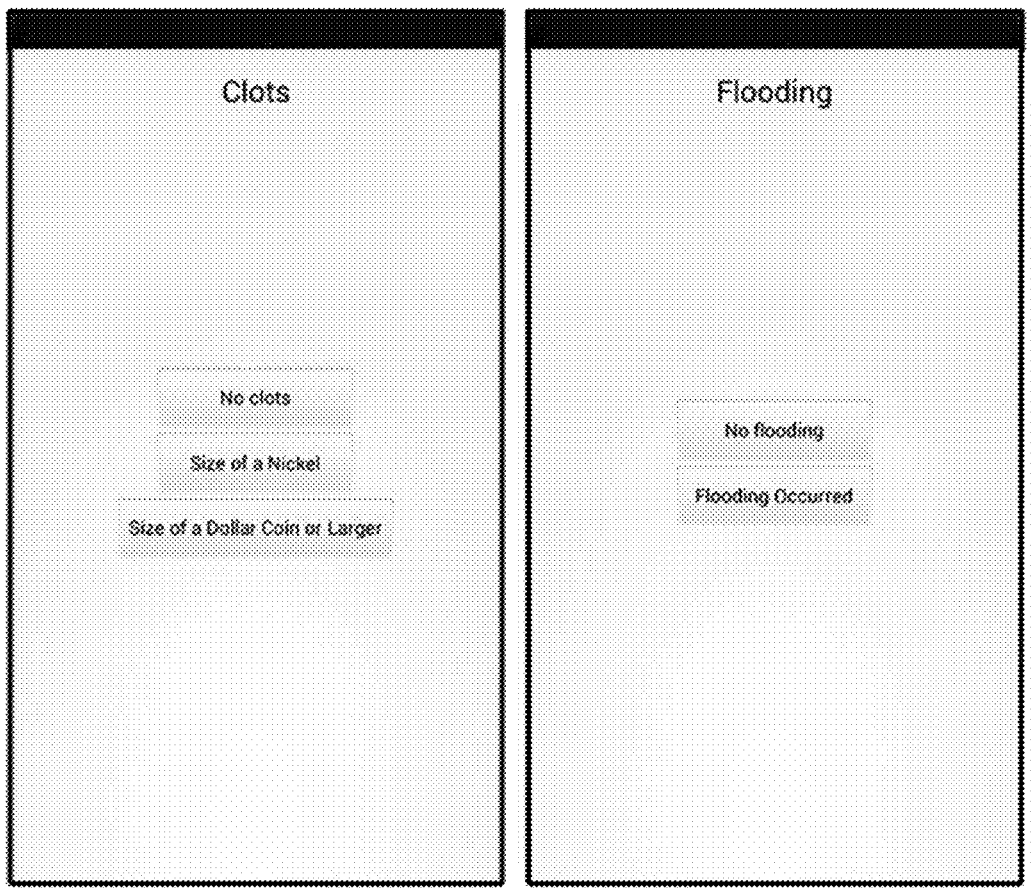

FIGS. 7G and 7H show screens in which the application is prompting the user for more information. In this example the user is asked to enter information relating to the existence and size of blood clots, as well as flooding. Other information may be collected from the patient as well, including symptoms, observations, etc.

Figure 7I:
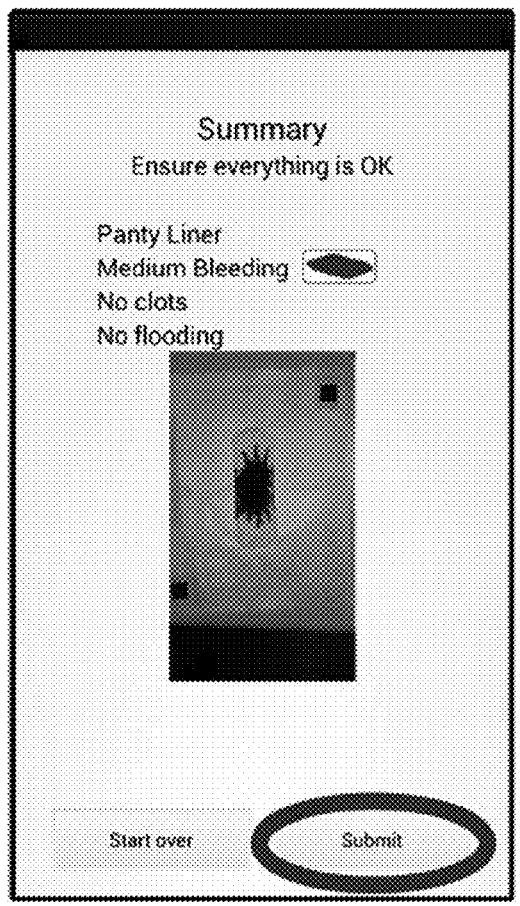

FIG. 7I shows a summary screen so that the user may review the information she has entered. The user may choose to enter the information or start the process over, or redo any of the steps. Once the information is submitted, the application may store the information, the application may submit the information to a server via a network, and/or the application may do analysis on the information submitted. Analysis of the information, including analysis of the image may be done on the client (i.e. the mobile device), on the server, or on a combination of the client and server. For example, encryption of the image and/or other information may be performed on the device before the information is uploaded to a server for further analysis, to preserve patient privacy.

In another example, some analysis of the image may be performed on the client, the application may analyze the image and present the user with information relating to the product type (for example, brand, type, size etc.) and the user may confirm or adjust this information before the image is uploaded to a server for any farther analysis. In another example, the application may alternatively analyze the image for acceptable quality before transferring the image to a server.

Figure 7J:

FIG. 7J shows a screen in which the application is asking the user whether she wants to record another product, or whether she wants to exit the application.

Figure 8:
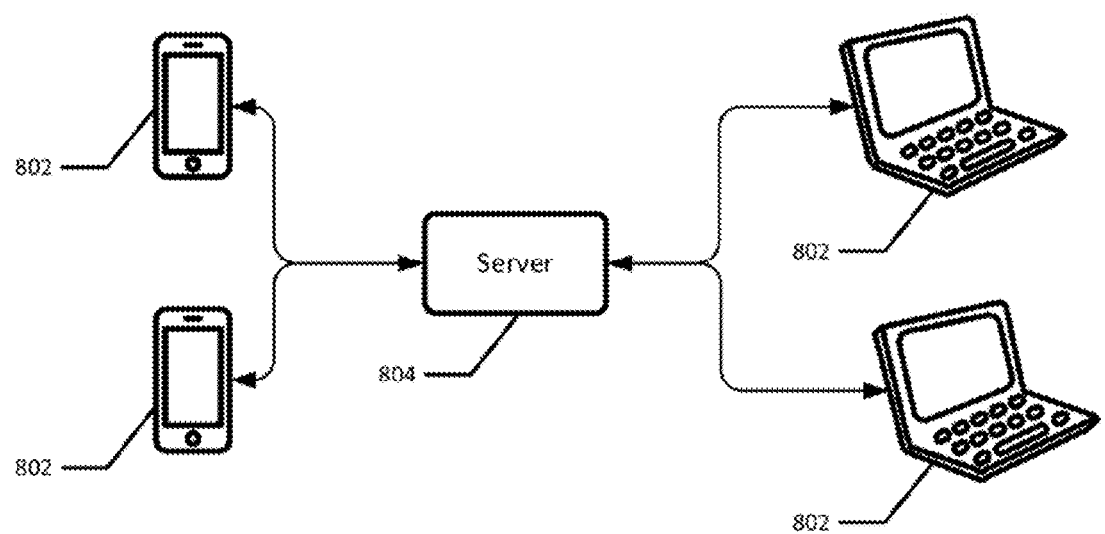
FIG. 8 shows a network diagram of an embodiment of a network.

FIG. 8 shows a possible configuration of the application of some embodiments. Application server 804 is connected to one or more clients 802. The connection may be via a network, for example a wired or wireless network, a Wi-Fi network, a Bluetooth network, or any other suitable network or combination of networks. The network may be the intranet, an intranet, a private network or any combination of networks. The server may include one or more computers and/or may be a series of more than one server. The server may include one or more databases. The server may include software and hardware.

The one or more clients may run on any suitable device or devices including mobile phones, tablets, smartphones, computers, laptop computers, desktop computers, etc. Client or clients 802 may include software, hardware or both. A client interface may include an application, web browser, other client or any combination thereof.

Clients 802 may be used by one or more patients, to upload images and data, and/or by one or more reviewers, to review images and data, and/or by one or more administrators to view and/or administrate a study, aggregate data and/or single patient data. The client, server, or both may perform analysis on the data.

In some embodiments, server 804 may be bypassed and the client may communicate directly with another client. For example, images and other data collected on handheld device 802 may be sent directly to a reviewer on a client computer. The client applications may be different on different client devices. Alternatively, a client 802, and server 804 may be combined in one device.

Figure 9:
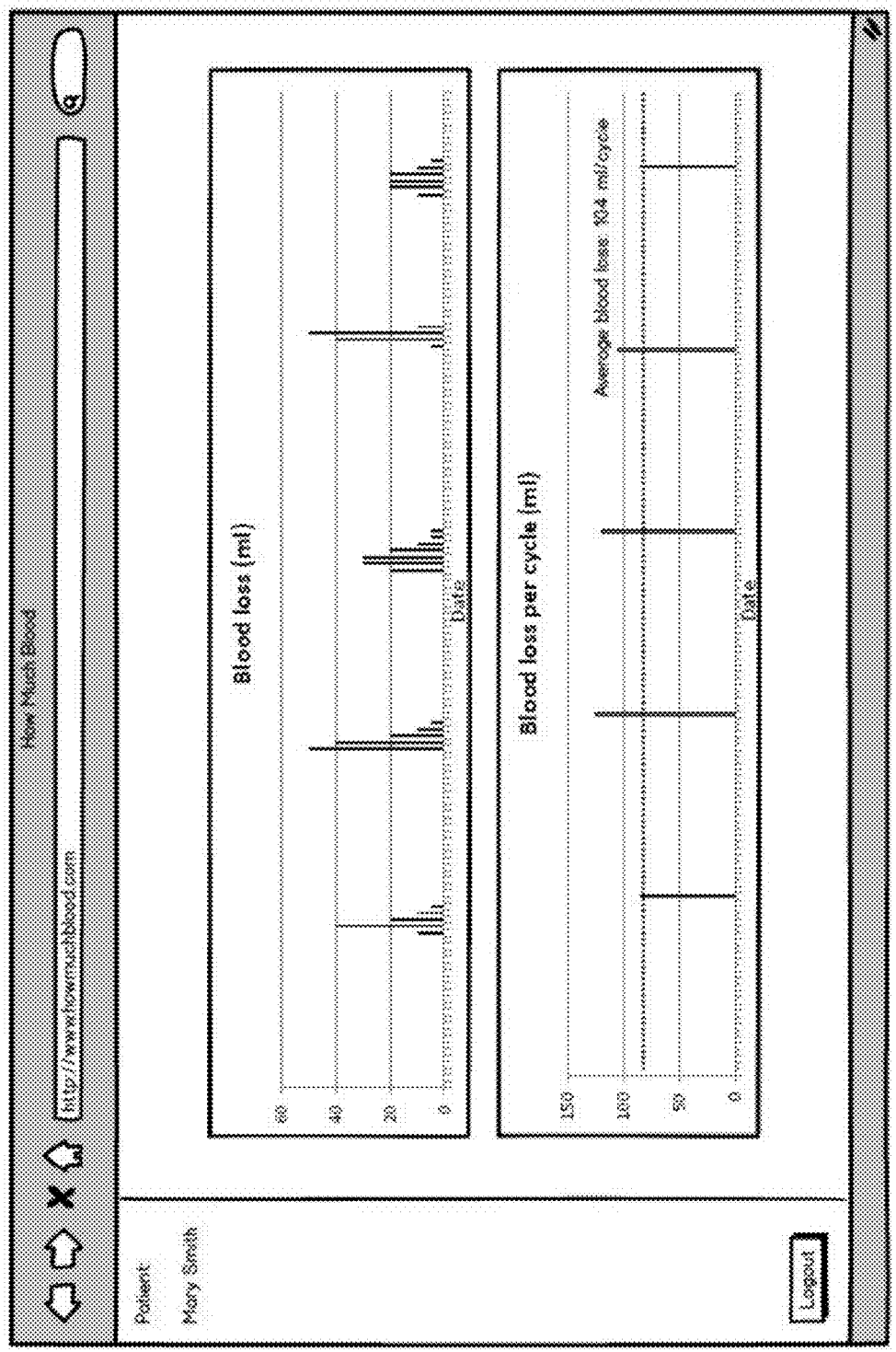
FIG. 9 shows a possible screenshot of an administrator screen.

FIG. 9 shows an embodiment where a patient, reviewer, and/or administrator may view the data. FIG. 9 represents an admin screen, in this example via a web browser, displaying some of the blood loss data. In this example, the application is displaying blood loss for one patient per day over time, blood loss per cycle over time, and average blood loss per cycle. Although this figure is showing data for one patient, data for multiple patients may be shown, including aggregated data and analysis results. More granular data can be viewed also. For example, if a user clicks on one of the bars in the top graph, the application may display the details behind that data point, including an image of used sanitary product, analysis of the image, clot info, flooding info, date and/or time info, sanitary product type info etc. If the graph were to represent aggregated patient data, drilling down on the graph might allow the user to view data for individual patients.

The application may also perform deeper analysis on the data, for example, analyzing trends. For example, the application might correlate blood loss with patient symptoms and display the results of the analysis to a user.

Figure 10:
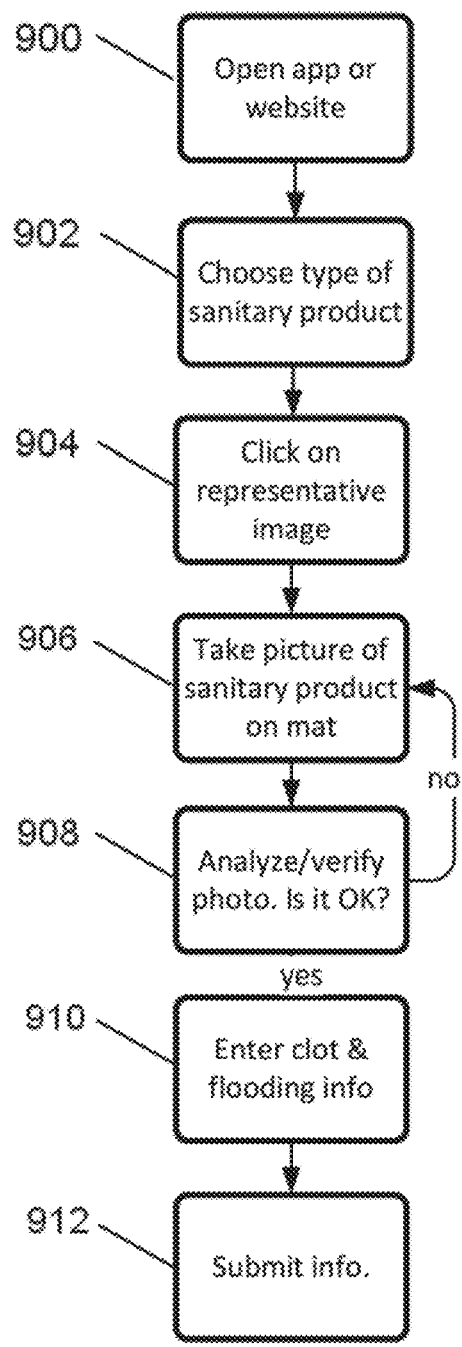
FIG. 10 shows a flow chart of an application from the user's perspective.

FIG. 10 shows some of the steps a user might go through when using the application. The user would first open the application or web site on her device 900, as is shown in FIG. 7A. The user would choose the type of sanitary product she wishes to enter 902, as is shown in FIG. 7B. Representative images, such as those shown in FIGS. 7C and 7D may be displayed to the user and the user may choose the image which best represents her used sanitary product 904. The user may then be prompted to take an image 906 of her used sanitary product, as is shown in FIG. 7E. The user then verifies the image, or, if the image is unacceptable, retakes the image 908, as is shown in FIG. 7F. The user then enters clot and flooding information 910 as is shown in FIGS. 7G and 7H. The user then submits the information 912 as is shown in FIG. 7I.

Figure 11:
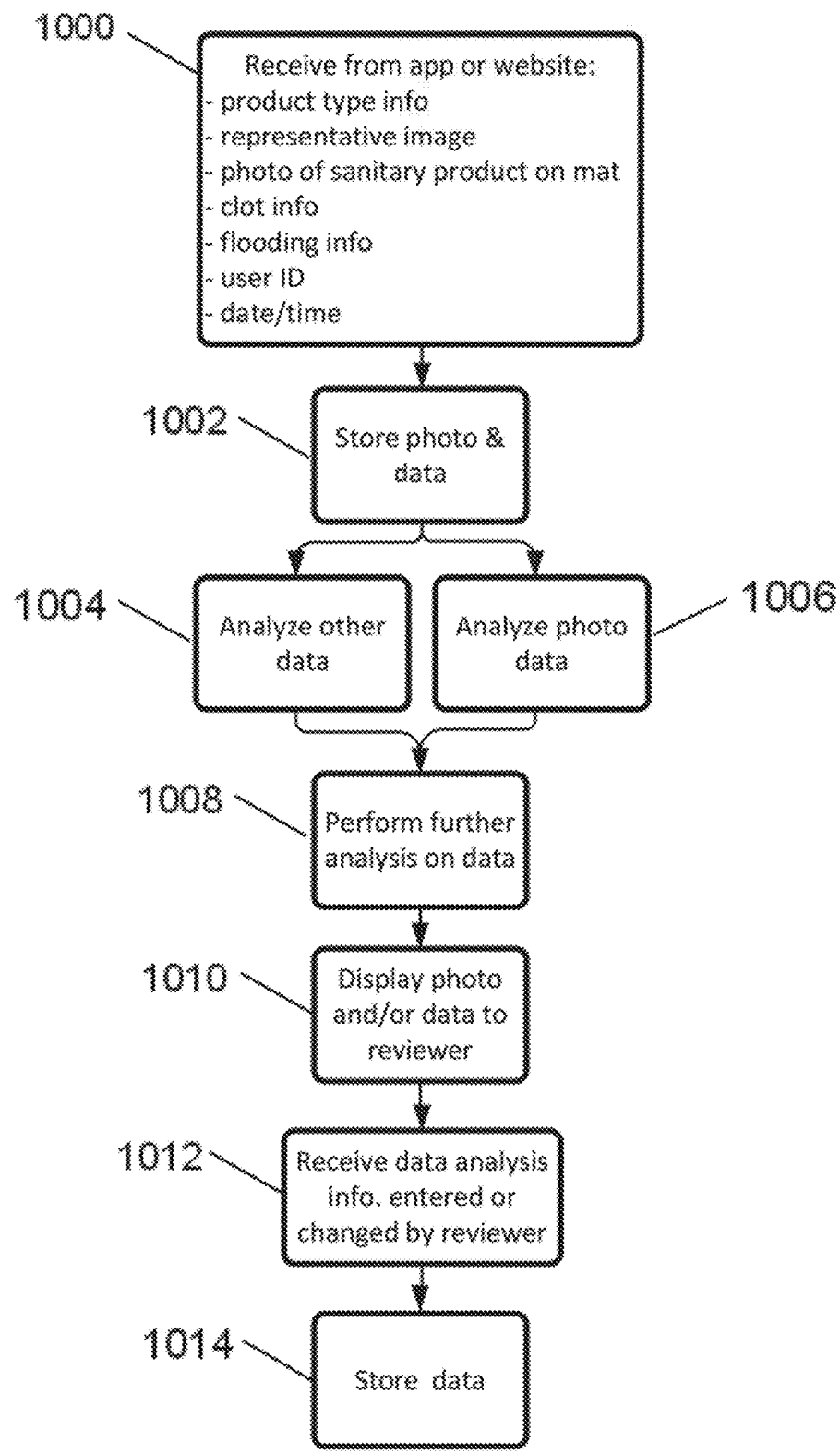
FIG. 11 shows a flow chart of an application from the server's perspective.

FIG. 11 shows how the application server operates in response to a user's actions. The server may receive from an application or a website on the user's device information 1000 including: product type information, a representative image, an image of the used sanitary product on a mat, clot related information, flooding related information and/or any other information, including user ID, date, time, etc. The application may receive some of this information or all of this information. The application may receive other information as well. The application may receive the information in one step or over 2 or more steps. The application may store the data 1002, possibly in a database, either on the same server computer or on another server computer.

The application may analyze the image and other data 1004, 1006, either with a user's interaction, or automatically, or both. The image may be analyzed 1008 using any appropriate technology including edge detection, convolution, deconvolution, object recognition, masking, subtraction, algebraic modification, Fourier transforms, averaging, and/or stain detection using color, color depth, color darkness/lightness or other thresholds, or any other image analysis technique. The application on the server may run these analyses automatically, or a user may help with the analysis, for example, by checking that the edges are appropriately detected and/or changing the edges as necessary. Alternatively, a reviewer may be prompted to review the image and/or other data 1010 and enter his/her analysis into the application 1012. The data, including any additional analysis information may be stored in the application server 1014.

Further analysis may also be performed after the data is stored. For example, trends may be ascertained over time and/or across patients. For example, blood loss may be tracked for a patient by menstrual cycle, over time, etc. The application may determine the blood loss for each image, add the volume of blood loss during a menstrual cycle to determine total blood loss during that cycle. Blood loss per cycle may also be aggregated to determine total blood loss over time, or average cycle blood loss over time.

Although FIG. 11 shows a server-based application, the same logic may be performed partly or entirely on a client. For example, the logic shown in FIG. 11 may be entirely or partially performed on a mobile device. The data may be stored on the mobile device, or it may be uploaded to a server either immediately, or at a later time.

Figure 12:
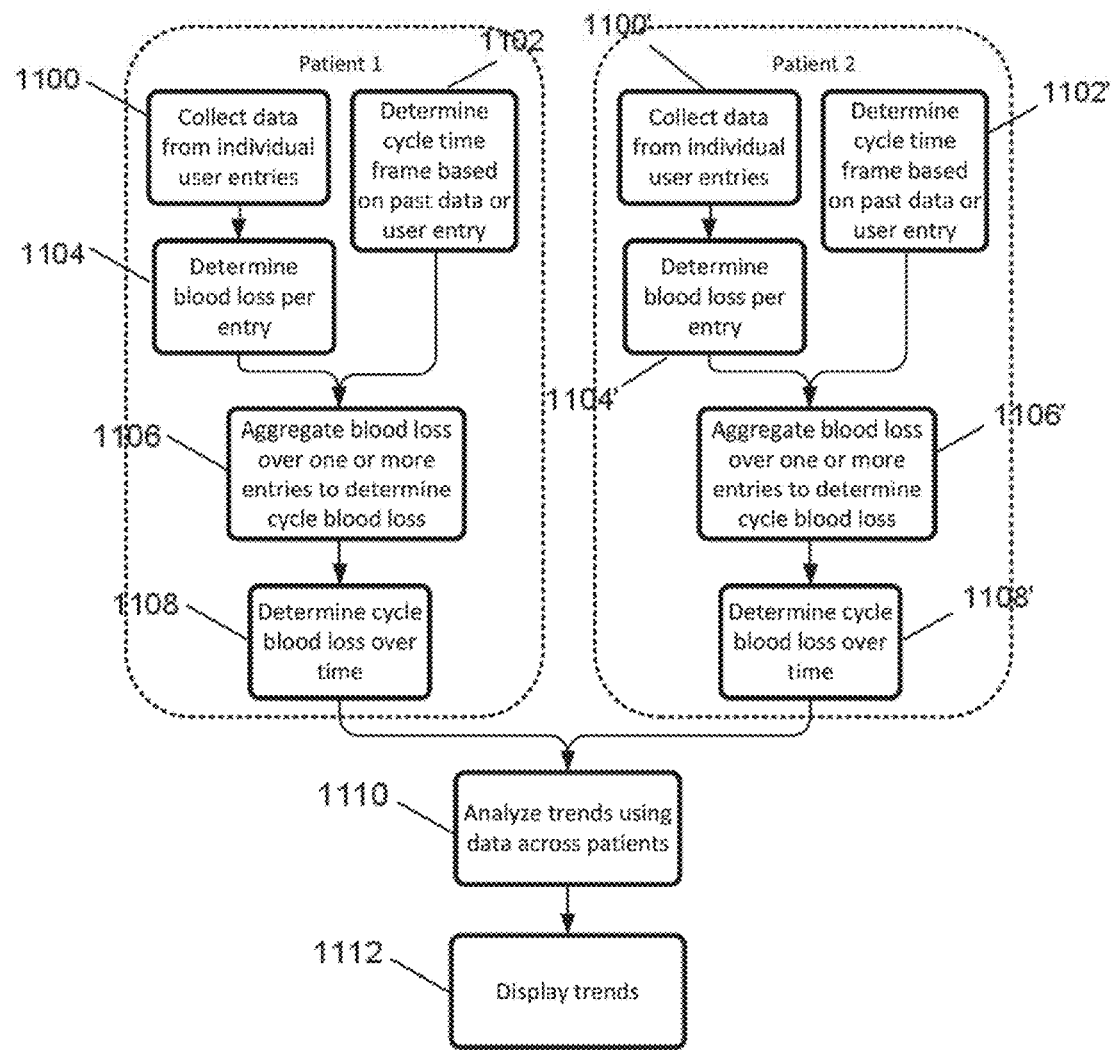
FIG. 12 shows a flow chart of possible analyses performed by the application.

FIG. 12 shows an example of how the application may analyze individual patient data and data across patients. Data is collected from individual users, or patients 1100, 1100' (e.g., Patient 1, Patient 2, etc.), as is shown in FIG. 11. In addition to collecting the data, the application may determine the patient's cycle, either by prompting the user to enter her cycle information, or by determining her cycle by analyzing blood loss data over time 1102, 1102'. For example, if the patient is submitting blood loss images and data on days 1-5, and then again on days 29-34 and then again on days 62-67, the application may determine that her cycle is 28 days in length. From this, the application may determine blood loss entries 1104, 1104' from day 14 of one cycle until day 14 of the next cycle and add these entries to determine total blood loss for that cycle 1106, 1106'. Note that blood loss for most of the days during the cycle will likely be zero. The application can also determine blood loss per cycle over time for a patient 1108, 1108'.

Because the application may collect data from more than one patient, data may be analyzed across patients and/or across time 1110. For example, the application may determine that cycles with blood loss over 80 ml correlate with cycles where blood clots over a certain size are reported. Using this data, the application may determine that blood clot size data correlates tightly to blood loss data and may be able to more accurately determine blood loss. Another example might include the application analyzing symptom data in connection with blood loss data. This type of analysis can be used to improve the application's logic, and/or to add to scientific knowledge in general. The application system can display these analytical results in graphs or other suitable formats 1112 for a user to review and manipulate.

Although embodiments discuss herein have focused on evaluating menstrual blood lost, other applications may also be applicable, including evaluating dressings, urinary incontinence, rashes, rosacea, varicose or spider or similar veins, shingles, chicken pox, fecal incontinence, surgery healing, insect bites, etc.

Example of Data Processing System

Figure 13:
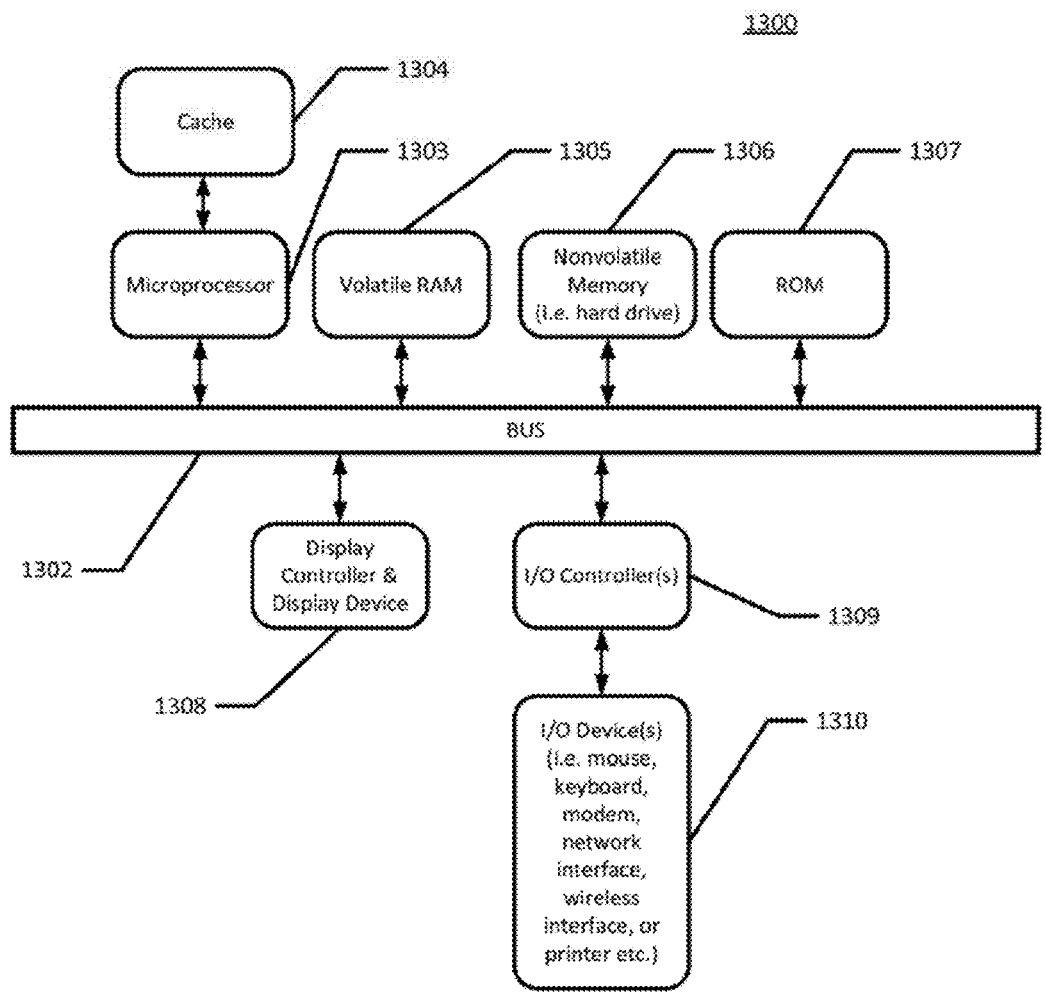
FIG. 13 is a block diagram of a data processing system, which may be used with any embodiments of the invention.

FIG. 13 is a block diagram of a data processing system, which may be used with any embodiment of the invention. For example, the system 1300 may be used as part of a server or a client as shown in FIG. 8. Note that while FIG. 13 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 13, the computer system 1300, which is a form of a data processing system, includes a bus or interconnect 1302 which is coupled to one or more microprocessors 1303 and a ROM 1307, a volatile RAM 1305, and a non-volatile memory 1306. The microprocessor 1303 is coupled to cache memory 1304. The bus 1302 interconnects these various components together and also interconnects these components 1303, 1307, 1305, and 1306 to a display controller and display device 1308, as well as to input/output (I/O) devices 1310, which may be mice, keyboards, modems, network interfaces, printers, and other devices which are well-known in the art.

Typically, the input/output devices 1310 are coupled to the system through input/output controllers 1309. The volatile RAM 1305 is typically implemented as dynamic RAM (DRAM) which requires power continuously in order to refresh or maintain the data in the memory. The non-volatile memory 1306 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 13 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1302 may include one or more buses connected to each other through various bridges, controllers, and/or adapters, as is well-known in the art. In one embodiment, the I/O controller 1309 includes a USB (Universal Serial Bus) adapter for controlling USB peripherals. Alternatively, I/O controller 1309 may include an IEEE-1394 adapter, also known as FireWire adapter, for controlling FireWire devices.

Some portions of the preceding detailed descriptions have been presented in terms of algorithms and symbolic representations of operations on data hits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

The invention claimed is:

1. A method for tracking menstrual blood loss volume, comprising:
   prompting a user to enter at least one input relating to a used sanitary product upon a first client device;
   capturing one or more images of the used sanitary product upon a mat with one or more markings, wherein the mat further comprises identifying information displayed upon the mat;
   receiving one or more images of the used sanitary product from the first client device;
   displaying the one or more images on a second client device;
   receiving the at least one input from the user via the second client device which includes an estimate of blood volume within or upon the sanitary product in the one or more images; and
   aggregating blood volume data from the one or more images to determine blood loss volume via a microprocessor for at least one menstrual cycle.

2. The method of claim 1 wherein the markings define a plurality of symbols uniformly or arbitrarily positioned upon the mat.

3. The method of claim 1 wherein the markings comprise a grid or scale.

4. The method of claim 1 wherein the markings comprises one or more concentric shapes.

5. The method of claim 1 wherein the markings comprise a plurality of patterns.

6. The method of claim 1 further comprising recording the one or more images of the used sanitary product via a mobile device.

7. The method of claim 1 wherein receiving one or more images comprises wirelessly receiving the one or more images.

8. The method of claim 1 wherein receiving the at least one input comprises prompting the user to select an image correlating to an amount of blood soaked within or upon the sanitary product.

9. The method of claim 1 wherein aggregating blood volume data comprises calculating the blood volume data via a microprocessor.

10. A method for tracking menstrual blood loss volume, comprising:
    prompting a user to enter at least one input relating to a used sanitary product upon a first client device;
    capturing the one or more images of the used sanitary product upon a mat with one or more markings, wherein the mat further comprises identifying information displayed upon the mat;
    receiving one or more images of the used sanitary product from the first client device;
    analyzing the one or more images via a microprocessor to estimate blood volume in the one or more images; and
    aggregating blood volume data from the one or more images to determine blood loss volume via the microprocessor for at least one menstrual cycle.

11. The method of claim 10 wherein the markings define a plurality of symbols uniformly or arbitrarily positioned upon the mat.

12. The method of claim 10 wherein the markings comprise a grid or scale.

13. The method of claim 10 wherein the markings comprises one or more concentric shapes.

14. The method of claim 10 wherein the markings comprise a plurality of patterns.

15. The method of claim 10 further comprising recording the one or more images of the used sanitary product via a mobile device.

16. The method of claim 10 wherein receiving one or more images comprises wirelessly receiving the one or more images.

17. The method of claim 10 wherein aggregating blood volume data comprises calculating the blood volume data via a microprocessor.

18. A method for tracking menstrual blood loss volume, comprising:
    prompting a user to enter at least one input relating to a used sanitary product upon a first client device;
    capturing one or more images of the used sanitary product upon a mat with one or more markings, wherein the markings comprise a textured surface;
    receiving one or more images of the used sanitary product from the first client device;
    displaying the one or more images on a second client device;
    receiving the at least one input from the user via the second client device which includes an estimate of blood volume within or upon the sanitary product in the one or more images; and
    aggregating blood volume data from the one or more images to determine blood loss volume via a microprocessor for at least one menstrual cycle.

19. The method of claim 18 wherein the markings define a plurality of symbols uniformly or arbitrarily positioned upon the mat.

20. The method of claim 18 wherein the markings comprise a grid or scale.

21. The method of claim 18 wherein the markings comprises one or more concentric shapes.

22. The method of claim 18 wherein the markings comprise a plurality of patterns.

23. The method of claim 18 further comprising recording the one or more images of the used sanitary product via a mobile device.

24. The method of claim 18 wherein receiving one or more images comprises wirelessly receiving the one or more images.

25. The method of claim 18 wherein receiving the at least one input comprises prompting the user to select an image correlating to an amount of blood soaked within or upon the sanitary product.

26. The method of claim 18 wherein aggregating blood volume data comprises calculating the blood volume data via a microprocessor.

27. A method for tracking menstrual blood loss volume, comprising:
prompting a user to enter at least one input relating to a used sanitary product upon a first client device;
receiving one or more images of the used sanitary product from the first client device;
displaying the one or more images on a second client device;
receiving the at least one input from the user via the second client device which includes an estimate of blood volume within or upon the sanitary product in the one or more images;
aggregating blood volume data from the one or more images to determine blood loss volume via a microprocessor for at least one menstrual cycle; and
receiving one or more images from a plurality of users.

28. The method of claim 27 wherein the markings define a plurality of symbols uniformly or arbitrarily positioned upon the mat.

29. The method of claim 27 wherein the markings comprise a grid or scale.

30. The method of claim 27 wherein the markings comprises one or more concentric shapes.

31. The method of claim 27 wherein the markings comprise a plurality of patterns.

32. The method of claim 27 further comprising recording the one or more images of the used sanitary product via a mobile device.

33. The method of claim 27 wherein receiving one or more images comprises wirelessly receiving the one or more images.

34. The method of claim 27 wherein receiving the at least one input comprises prompting the user to select an image correlating to an amount of blood soaked within or upon the sanitary product.

35. The method of claim 27 wherein aggregating blood volume data comprises calculating the blood volume data via a microprocessor.

36. A method for tracking menstrual blood loss volume, comprising:
prompting a user to enter at least one input relating to a used sanitary product upon a first client device;
receiving one or more images of the used sanitary product from the first client device;
displaying the one or more images on a second client device;
receiving the at least one input from the user via the second client device which includes an estimate of blood volume within or upon the sanitary product in the one or more images;
aggregating blood volume data from the one or more images to determine blood loss volume via a microprocessor for at least one menstrual cycle; and
analyzing the blood volume data for trending information.

37. The method of claim 36 wherein the markings define a plurality of symbols uniformly or arbitrarily positioned upon the mat.

38. The method of claim 36 wherein the markings comprise a grid or scale.

39. The method of claim 36 wherein the markings comprises one or more concentric shapes.

40. The method of claim 36 wherein the markings comprise a plurality of patterns.

41. The method of claim 36 further comprising recording the one or more images of the used sanitary product via a mobile device.

42. The method of claim 36 wherein receiving one or more images comprises wirelessly receiving the one or more images.

43. The method of claim 36 wherein receiving the at least one input comprises prompting the user to select an image correlating to an amount of blood soaked within or upon the sanitary product.

44. The method of claim 36 wherein aggregating blood volume data comprises calculating the blood volume data via a microprocessor.

45. A method for tracking menstrual blood loss volume, comprising:
prompting a user to enter at least one input relating to a used sanitary product upon a first client device;
capturing the one or more images of the used sanitary product upon a mat with one or more markings, wherein the markings comprise a textured surface;
receiving one or more images of the used sanitary product from the first client device;
analyzing the one or more images via a microprocessor to estimate blood volume in the one or more images; and
aggregating blood volume data from the one or more images to determine blood loss volume via the microprocessor for at least one menstrual cycle.

46. The method of claim 45 wherein the markings define a plurality of symbols uniformly or arbitrarily positioned upon the mat.

47. The method of claim 45 wherein the markings comprise a grid or scale.

48. The method of claim 45 wherein the markings comprises one or more concentric shapes.

49. The method of claim 45 wherein the markings comprise a plurality of patterns.

50. The method of claim 45 further comprising recording the one or more images of the used sanitary product via a mobile device.

51. The method of claim 45 wherein receiving one or more images comprises wirelessly receiving the one or more images.

52. The method of claim 45 wherein aggregating blood volume data comprises calculating the blood volume data via a microprocessor.

53. A method for tracking menstrual blood loss volume, comprising:
prompting a user to enter at least one input relating to a used sanitary product upon a first client device;
receiving one or more images of the used sanitary product from the first client device;
analyzing the one or more images via a microprocessor to estimate blood volume in the one or more images;
aggregating blood volume data from the one or more images to determine blood loss volume via the microprocessor for at least one menstrual cycle; and
receiving one or more images from a plurality of users.

54. The method of claim 53 wherein the markings define a plurality of symbols uniformly or arbitrarily positioned upon the mat.

55. The method of claim 53 wherein the markings comprise a grid or scale.

56. The method of claim 53 wherein the markings comprises one or more concentric shapes.

57. The method of claim 53 wherein the markings comprise a plurality of patterns.

58. The method of claim 53 further comprising recording the one or more images of the used sanitary product via a mobile device.

59. The method of claim 53 wherein receiving one or more images comprises wirelessly receiving the one or more images.

60. The method of claim 53 wherein aggregating blood volume data comprises calculating the blood volume data via a microprocessor.

61. A method for tracking menstrual blood loss volume, comprising:

prompting a user to enter at least one input relating to a used sanitary product upon a first client device;

receiving one or more images of the used sanitary product from the first client device;

analyzing the one or more images via a microprocessor to estimate blood volume in the one or more images;

aggregating blood volume data from the one or more images to determine blood loss volume via the microprocessor for at least one menstrual cycle; and analyzing the blood volume data for trending information.

62. The method of claim 61 wherein the markings define a plurality of symbols uniformly or arbitrarily positioned upon the mat.

63. The method of claim 61 wherein the markings comprise a grid or scale.

64. The method of claim 61 wherein the markings comprises one or more concentric shapes.

65. The method of claim 61 wherein the markings comprise a plurality of patterns.

66. The method of claim 61 further comprising recording the one or more images of the used sanitary product via a mobile device.

67. The method of claim 61 wherein receiving one or more images comprises wirelessly receiving the one or more images.

68. The method of claim 61 wherein aggregating blood volume data comprises calculating the blood volume data via a microprocessor.

* * * * *